(12) United States Patent
Bentz et al.

(10) Patent No.: US 10,131,133 B2
(45) Date of Patent: Nov. 20, 2018

(54) METHODS FOR FORMING OPTICALLY HETEROGENEOUS PHANTOM STRUCTURES AND PHANTOM STRUCTURES FORMED THEREBY

(71) Applicant: Purdue Research Foundation, West Lafayette, IN (US)

(72) Inventors: Brian Zahler Bentz, Albuquerque, NM (US); Kevin J Webb, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/782,179

(22) Filed: Oct. 12, 2017

(65) Prior Publication Data

US 2018/0104946 A1   Apr. 19, 2018

Related U.S. Application Data

(60) Provisional application No. 62/409,028, filed on Oct. 17, 2016.

(51) Int. Cl.
*G01D 18/00* (2006.01)
*B33Y 80/00* (2015.01)
(Continued)

(52) U.S. Cl.
CPC .............. *B33Y 80/00* (2014.12); *A61B 6/583* (2013.01); *B29C 64/129* (2017.08); *B29C 64/40* (2017.08);
(Continued)

(58) Field of Classification Search
CPC ..... G06T 11/003; G09B 23/30; G09B 23/303; G01N 21/278; G01N 33/49
See application file for complete search history.

(56) References Cited

U.S. PATENT DOCUMENTS

| | | | |
|---|---|---|---|
| 2004/0067591 A1* | 4/2004 | Madsen | A61B 5/055 436/8 |
| 2005/0145786 A1* | 7/2005 | Rice | A61B 5/0073 250/252.1 |

(Continued)

FOREIGN PATENT DOCUMENTS

| | | | | |
|---|---|---|---|---|
| WO | WO 2016137425 A1 * | 9/2016 | | A61B 6/583 |
| WO | WO 2017049380 A1 * | 3/2017 | | G09B 23/30 |

OTHER PUBLICATIONS

Nguyen T.; Le, H.; Vo, M.; Wang, Z.; Luu, L.; Ramella-Roman, J., "Three-dimensional phantoms for curvature correction in spatial frequency domain imaging", Biomedical Optics Express, 2012, vol. 3, No. 6, pp. 1200-1214.

(Continued)

*Primary Examiner* — Kiho Kim
(74) *Attorney, Agent, or Firm* — Purdue Research Foundation

(57) ABSTRACT

An optically heterogeneous phantom structure for use in optical imaging techniques. The phantom structure includes an external shape simulating an object to be subjected to an optical imaging technique, the external shape defining an external surface that encloses an internal volume of the external shape; and an optically heterogeneous material filling the internal volume and having heterogeneous optical properties for simulating at least one optical parameter of at least one region within the object. A method of producing the optically heterogeneous phantom structure. The method includes selectively depositing precursors of a first material and a second material by 3D printing so that the precursor of the second material is surrounded by the precursor of the first material within a predetermined internal region of the precursor of the first material, and forming the phantom structure. Variations of the method include additives to the materials.

22 Claims, 10 Drawing Sheets

True inhomogeneity location

Reconstructed absorption inhomogeneity

Isosurfaces showing the absorption inhomogeneity

(51) Int. Cl.
  *B33Y 10/00* (2015.01)
  *B29C 64/129* (2017.01)
  *A61B 6/00* (2006.01)
  *B29C 64/40* (2017.01)
  *G06T 11/00* (2006.01)
  *B29L 31/40* (2006.01)
  *H04N 5/372* (2011.01)

(52) U.S. Cl.
  CPC ...... *B33Y 10/00* (2014.12); *B29K 2995/0026* (2013.01); *B29L 2031/40* (2013.01); *G06T 11/003* (2013.01); *H04N 5/372* (2013.01)

(56) References Cited

U.S. PATENT DOCUMENTS

| 2005/0187478 | A1* | 8/2005 | Beaudry | A61B 5/0091 |
| | | | | 600/476 |
| 2007/0200058 | A1* | 8/2007 | Rice | A61B 5/0071 |
| | | | | 250/252.1 |
| 2010/0210931 | A1* | 8/2010 | Cuccia | A61B 5/0059 |
| | | | | 600/328 |
| 2014/0003692 | A1* | 1/2014 | Yared | A61B 5/0073 |
| | | | | 382/131 |
| 2015/0320394 | A1* | 11/2015 | Arnal | G01S 7/52079 |
| | | | | 600/427 |
| 2016/0370285 | A1* | 12/2016 | Jang | G01N 21/278 |
| 2017/0291359 | A1* | 10/2017 | Kerins | B29C 67/0059 |
| 2018/0116724 | A1* | 5/2018 | Gmeiner | A61B 34/10 |

OTHER PUBLICATIONS

Gerhard, M.; Kolzer, J.; Otto J.; Plies, E.; Solkner, G.; Zinth, W., "Time-gated transillumination of biological tissues and tissuelike phantoms", Applied Optics, 1994, vol. 33, No. 28, pp. 6699-6710.

Wang, J.; Coburn, J.; Liang, C.; Woolsey, N.; Ramella-Roman, J.,; Chen, Y.; Pfefer J.; "Three-dimensional printing of tissue phantoms for biophotonic imaging", Optics Letters, 2014, vol. 39, No. 10, pp. 3010-3013.

* cited by examiner

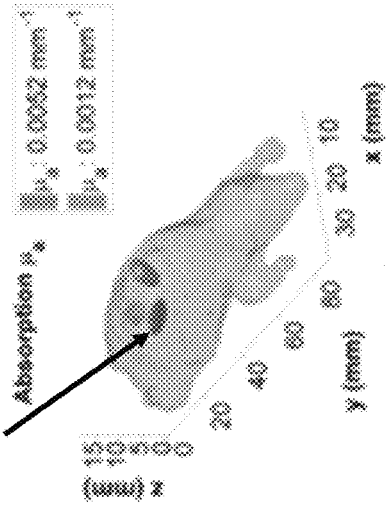
FIG. 5A
FIG. 5B
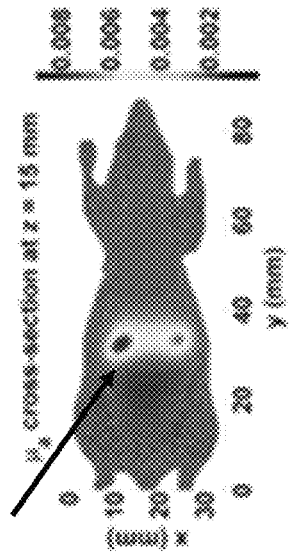
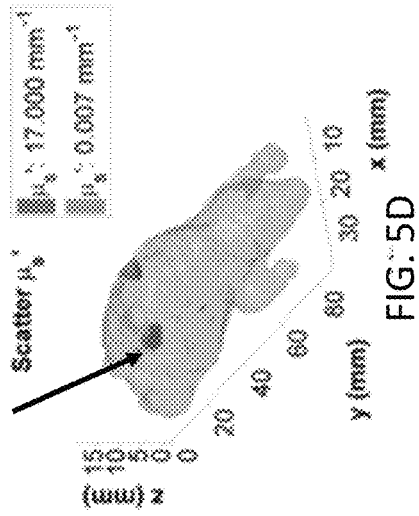
FIG. 5C
FIG. 5D
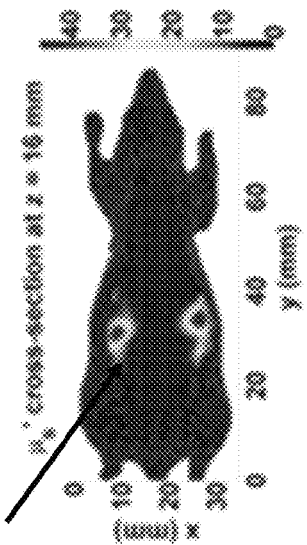

Surface profile used to fabricate a mouse phantom.

Inhomogeneity

Contrast agents are placed in the cavity to create an inhomogeneous phantom.

Cover piece

Homogeneous phantom for calibration

METHODS FOR FORMING OPTICALLY HETEROGENEOUS PHANTOM STRUCTURES AND PHANTOM STRUCTURES FORMED THEREBY

CROSS-REFERENCE TO RELATED APPLICATIONS

The present U.S. patent application is related to and claims the priority benefit of U.S. Provisional Patent Application Ser. No. 62/409,028, filed Oct. 17, 2016, the contents of which hereby incorporated by reference in their entirety into the present disclosure.

STATEMENT REGARDING GOVERNMENT FUNDING

This invention was made with government support under CA182235 awarded by the National Institutes of Health and CISE1218909 and CBET0854249 awarded by the National Science Foundation. The government has certain rights in the invention.

TECHNICAL FIELD

The present invention generally relates to imaging techniques and materials used therewith. The invention particularly relates to three-dimensional (3D) printing processes capable of producing 3D articles that are useful in optical imaging techniques, for example, of types that may be used in biomedical applications.

BACKGROUND

This section introduces aspects that may help facilitate a better understanding of the disclosure. Accordingly, these statements are to be read in this light and are not to be understood as admissions about what is or is not prior art. For the purposes of this disclosure, "optically heterogeneous" means a heterogeneous structure where the heterogeneity leads to differences in optical or related properties.

A variety of optical imaging techniques can be used, for example, in biomedical applications. For example, microscopy methods (MM) and optical coherence tomography (OCT) allow imaging at shallow depths in tissue. In deep tissue, the deleterious effects of scatter require different techniques, such as diffuse optical imaging (DOI) (also known as optical diffusion imaging), where a model of scattered light propagation can assist with image formation. DOI techniques may encompass such imaging methods as hyperspectral reflectance imaging (HRI), speckle imaging, spatial frequency domain imaging (SFDI), diffuse optical tomography (DOT), optical diffusion tomography (ODT), near infrared optical tomography (NIROT), fluorescence diffuse optical tomography (FDOT), and fluorescence optical diffusion tomography (FODT). DOI techniques use light of certain wavelengths to penetrate a body and the tissue portion thereof and form 3D images of the tissue as a result of light scattering and absorption that occurs when inhomogeneities are encountered. Optical imaging techniques can be utilized to obtain information regarding medical conditions and biological activities within living bodies, including conditions and activities of such internal organs as the heart, brain, kidneys, lungs, liver, skeleton, vascular structures, etc.

Imaging techniques and equipment typically require testing and calibration to promote the reliability of their results. For this purpose, optical imaging techniques often involve the fabrication of a "phantom" structure intended to simulate an object of interest, such as an entire body or portion thereof to be evaluated with the imaging technique. Phantoms are particularly useful for calibrating imaging techniques that will be used to evaluate tissue of a living body, as they avoid the need to have actual tissue for calibration, for example, a tissue donor, live subject, cadaver, etc. Consequently, a phantom is preferably fabricated to emulate internal and external physical characteristics of a body and its tissue. In order to do so, a phantom should have controlled optical properties, including but not limited to regions in which the phantom has different scattering, absorption, or fluorescent properties.

Phantoms can be formed of polymeric materials that contain additives intended to adjust its optical properties. External geometry and physical characteristics of the body to be simulated by a phantom are emulated by the mold in which the phantom is formed, whereas internal physical characteristics of, for example, tissue within the body are emulated by attempting to control the optical properties within the phantom with additives that alter the scattering and/or absorption and/or related optical coefficients of the phantom material. These injection molding techniques typically used in the fabrication of phantoms may adequately simulate the external shape of a body, but difficulties arise if the body has a complex external shape. Furthermore, injection molding techniques are not well suited for controllably tuning the internal physical characteristics of a phantom by selectively placing additives in regions that alter the scattering and/or absorption and/or related optical coefficients of the phantom to accurately simulate inhomogeneities such as internal organs.

Thus there is unmet need for phantoms that accurately simulate inhomogeneities of interest within a background medium. The methods detailed within this disclosure are meant to satisfy this unmet need.

SUMMARY

An optically heterogeneous phantom structure for use in optical imaging techniques is disclosed. The phantom structure includes an external shape simulating an object to be subjected to an optical imaging technique, the external shape defining an external surface that encloses an internal volume of the external shape; and an optically heterogeneous material filling the internal volume and having heterogeneous optical properties for simulating at least one optical parameter of at least one region within the object, the optically heterogeneous material comprising at least first and second materials having different optical properties, the second material being surrounded by at least the first material and simulating inhomogeneities of the object, wherein at least one of the at least first and second materials contains at least a first additive so as to so as to have at least one optical parameter that is different for the first material and the second material. Further, the phantom structure is formed by 3D printing to sequentially form the external shape of the phantom structure a layer at a time, to be substantially watertight at the external surface thereof, and to be substantially free of air gaps within the internal volume thereof.

A method of producing the optically heterogeneous phantom structure is disclosed. The method includes selectively depositing precursors of a first material and a second materials by 3D printing so that the precursor of the second material is surrounded by the precursor of the first material within a predetermined internal region of the precursor of the first material, and forming the phantom structure by a a 3D printing process and curing the precursors of the first and second materials so that the second material simulates optical properties of the region within the object. In a variant of this method, at least one material contains at least a first additive so as to have at least one optical parameter that is different from the other material(s).

BRIEF DESCRIPTION OF DRAWINGS

While some of the figures shown herein may have been generated from scaled drawings or from photographs that are scalable, it is understood that such relative scaling within a figure are by way of example, and are not to be construed as limiting.

FIG. 5A shows a $\mu_a$ mesh cross section from the reconstructed image at the z=15 mm plane.

FIG. 5B shows isosurfaces generated using the $\mu_a$ image. The kidneys are clearly visible.

FIG. 5C shows a $\mu'_s$ mesh cross section from the reconstructed image at the z=16 mm plane.

FIG. 5D shows isosurfaces generated using the $\mu'_s$ image. The kidneys are clearly visible.

DETAILED DESCRIPTION

Figure 1:
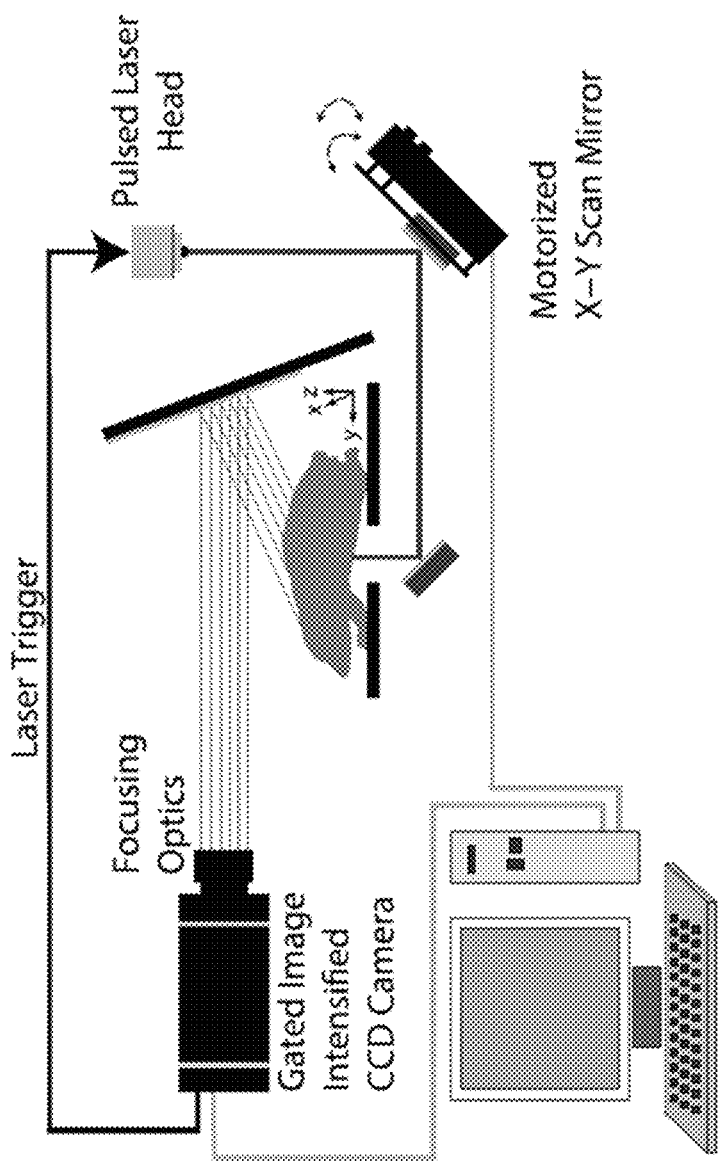
FIG. 1 is a schematic representation of a non-limiting experimental setup used to collect data for optical imaging. Pulsed time-domain data transmitted through the subject (shown here as a mouse) is captured by a gated, intensified CCD camera. A motorized X-Y scan mirror changes the source position before each gated measurement. A computer is used to control the camera and the motorized X-Y stage, automating the data capture

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended.

The present invention encompasses methods for fabricating phantoms suitable for use in optical imaging techniques that enable the accurate selection and tuning of optical properties (for example, scatter and absorption coefficients) of the phantoms. The methods employ 3D printing to form the external shape and surfaces (geometry) of a phantom, enabling the fabrication of phantoms with complex internal and external geometries. As understood in the art, 3D printing is an additive manufacturing (AM) process that entails forming a solid three-dimensional net or near-net-shape (NNS) object by sequentially forming the shape of the object one layer at a time. One particular 3D printing technique of interest utilizes an energy beam, for example, an electron beam or electromagnetic radiation such as a laser beam, to cure a curable photopolymeric material, and integrate the use of computer aided design (CAD) models to produce objects having complex geometries. Commercial 3D printers capable of printing more than one material are common, and 3D printing technology is rapidly improving.

Preferred materials for use in the 3D printing methods include clear (transparent or translucent) photopolymer resins as a base material, which may be combined with controlled amounts of one or more materials ("additive") that when combined with the base material result in a mixture composition that has one or more optical properties that are different from the resin, for example, by having a higher or lower optical scatter, absorption, and/or fluorescent yield coefficient. A nonlimiting example of a suitable clear photopolymer resin is a mixture of methacrylic acid esters and a photoinitiator. Acrylonitrile butadiene styrene (ABS) is another common material used in 3D printing. Nonlimiting examples of suitable "scattering agents" include polystyrene micro spheres and lipid or fat emulsions such as Intralipid. Nonlimiting examples of suitable "absorption agents" include nigrosin and India ink. Nonlimiting examples of suitable "fluorescing agents" include fluorescent proteins and quantum dots. The base material and one or more mixture compositions are printed layer by layer with a suitable 3D printer so that the mixture compositions are deposited at one or more predetermined locations within the base material, and the base material and mixture compositions are cured to form a phantom in which the cured mixture composition is located within predetermined internal regions of the phantom. Appropriate amounts of the agents for attaining desired optical properties within the predetermined internal regions may be calculated analytically using Mie theory or determined empirically. The optical properties of a phantom may be tailored to have at least one internal region with controlled optical properties that are, for example, similar to tissue of one or more organs within a living body, resulting in a phantom that can be useful for developing biomedical optical imaging modalities. As a result of 3D printing a phantom with multiple materials, at least two of which having different optical properties, the phantom can be made heterogeneous, allowing for the placement of complex inhomogeneities in a complex geometry, which is ideal for testing, evaluating, developing, and calibrating imaging methods and equipment.

Stereolithography is one non-limiting example of a 3D printing process or method for producing the optically heterogeneous phantom. An aspect of the method of this disclosure is that, by utilizing stereolithography, the resulting phantom can be formed to be substantially if not completely watertight at its external surface, and substantially if not completely free of air gaps within its internal volume. Such a possibility is in contrast to phantoms that are 3D printed from ABS using fused-deposition modeling.

Non-limiting experimental investigations and results leading up to the invention are described in more detail in the following description.

In experiments leading to this disclosure, reproducible heterogeneous solid phantoms were fabricated using a 3D printer. A popular publicly available whole body mouse atlas called Digimouse was used to print realistic phantoms in the shape of mice from acrylonitrile butadiene styrene (ABS-used in Lego blocks), which has optical scatter and absorption characteristics similar to tissue. It should be noted that in this disclosure the term "Digimouse" is also used to denote the surface profile of a mouse or an object or a phantom structure. Those skilled in the art will be able to tell whether the term Digimouse refers to the atlas and/or the platform used toc rate the structures or to the structures or, surfaces or phantoms themselves depending on the context. Digimouse was constructed from coregistered x-ray, computed tomography (CT), and cryosection data of a normal nude male mouse and contains information on the geometrical structure of all major organs, fundamentally allowing a complete phantom to be printed from multiple materials which match the optical characteristics of the respective organs. Two inhomogeneities were printed in the shape and at the location of the kidneys using two materials. Experimental data were captured and images were reconstructed with DOT using the open source TOAST++ package.

Data in the form of boundary measurements of light intensity as a function of space and time were captured from the printed mice for image reconstruction using the automated set up shown in FIG. 1. Referring to FIG. 1, a 633 nm pulsed laser was used as the source and a cooled, gated, image-intensified CCD camera (Roper PIMAX, 512×512 pixels) was used for detection. A 3D topography laser line scanner was used to obtain the 3D profile of the printed mice, and this 3D profile was used to determine the detector positions by projecting the CCD camera pixels to the phantom surface. The position of the source was controlled using an X-Y motorized mirror mount from Zaber (T-MM2-KT04U), and the 3D topography scan was controlled using a 150 mm motorized linear stage, also from Zaber (T-LSM150A-KT04U). The microstep size of the X-Y mirror mount is 0.000086°, and the microstep size of the linear stage is 0.0476 μm. A script was written to control the stages and the camera for both the 3D scan and the gated measurement, fully automating the experiment. This automation not only allowed for much faster acquisition of the data but also better repeatability of the source positions for imaging the various printed mice. Gated transmission data were collected from the printed mice using a gate width of 1.56 ns and 80,000 gates with a sequential delay that varied from 17 to 35 ns for 41 images, where 17 ns is the delay required for the laser pulse triggered by the camera controller to reach the camera. The laser has an energy per pulse of 12 pJ and was triggered at 5000 Hz by the camera, giving an average power of 60 nW.

3D Printing is an additive process by which material is added layer by layer to build an object. We used the MakerBot Replicator 2X, allowing us to print an object from two different materials. The printer operates by extruding ABS (acrylonitrile butadiene styrene) through two heated Teflon-coated nozzles (on the bottom of the extruders) onto a heated build plate. The nozzles' horizontal position is controlled by two stepper motors, and the plate is translated vertically to allow printing in three dimensions. For a typical print, a 3D profile is generated in a computer-aided design (CAD) program and converted to standard tessellation language (STL) format, which describes the raw unstructured triangulated surface by the unit normals and vertices of the surface triangles in Cartesian coordinates. This 3D surface profile is "sliced" by the MakerBot software and converted to ×3g format, which uses g-code to control the 3D printer. The ×3 g file is loaded into the printer using a secure digital (SD) card.

The quality of the print is influenced by many setup parameters, including motor speed, nozzle temperature, layer thickness, and the temperature and leveling of the build plate. For our optical phantom, we printed at 100% fill with two materials, which required optimizing these parameters, known to those skilled in the art, to achieve a successful print.

Figure 2:
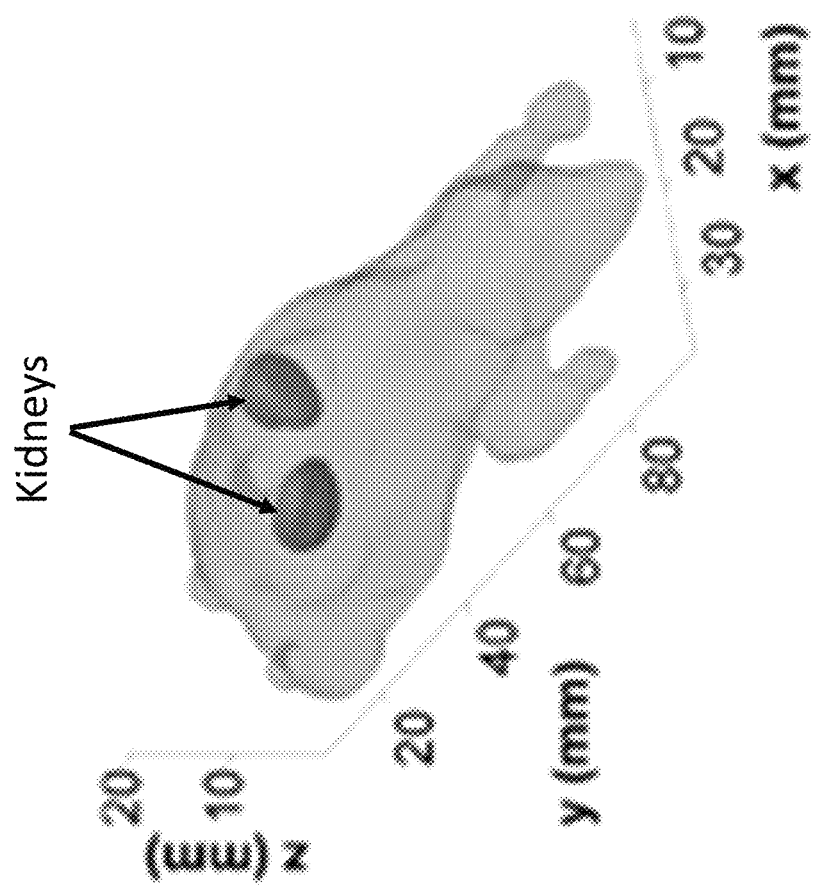
FIG. 2 shows a surface profile used to fabricate a mouse phantom, as a non-limiting design of the phantom geometry. An isosurface was formed using the Digimouse atlas and used to fabricate the mouse phantom for optical imaging. The inhomogeneities of interest were the kidneys.

The Digimouse mouse atlas contains data on the geometrical structure of the major organs of a normal nude male mouse at a resolution of 0.1 mm. The data is organized in a Cartesian grid and consists of integers corresponding to different organs or types of tissue. By computationally scanning through this data, only the kidneys and the skin of the Digimouse were selected and used to create a surface profile, which was then converted to an STL file in MAT-LAB for 3D printing. FIG. 2 shows the resulting Digimouse isosurface with the kidneys. It should be recognized that more organs, such as brain, heart, lungs, liver, skeleton, etc. can be included in the print, but in this described experiment, only the kidneys were printed. It should also be recognized that, in some situations, each organ could be printed from a different material with optical properties similar to the actual tissue. Finally, it should be recognized that the spatial scale of the phantom could be changed, and that much larger or much smaller phantoms could be fabricated, as required by the imaging modality.

Figure 3:
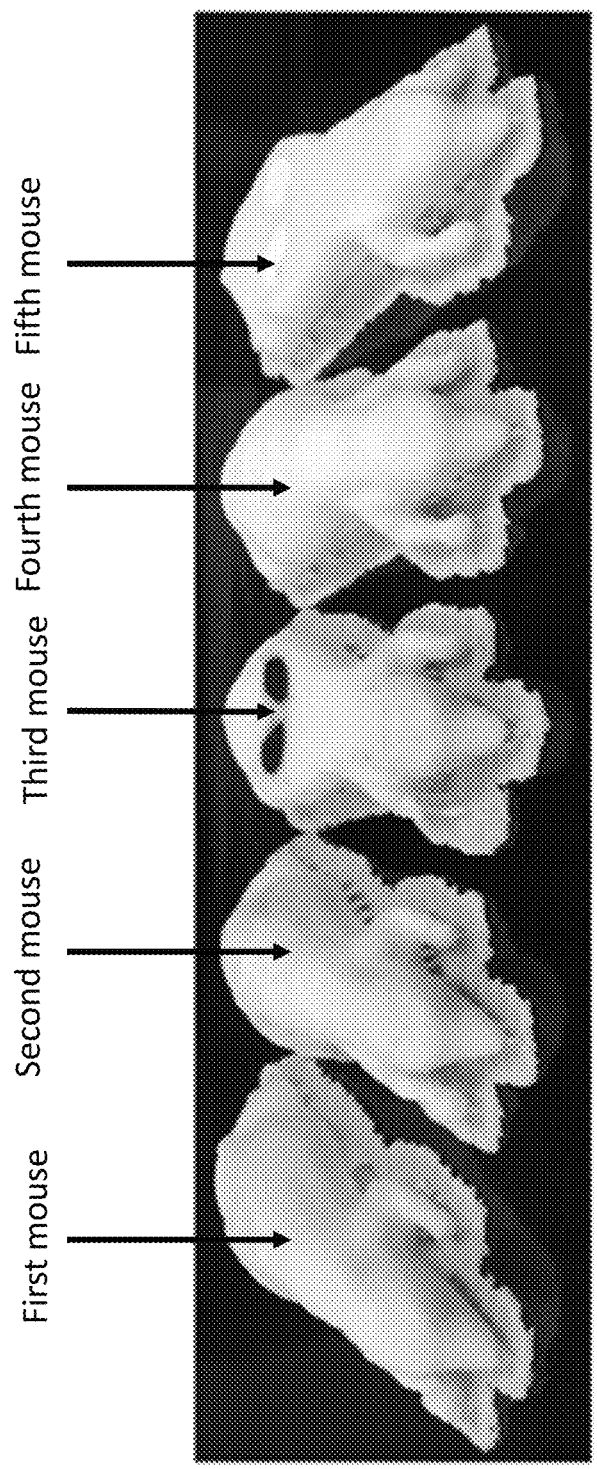
FIG. 3 shows the mouse phantoms that were fabricated using the isosurface designed in FIG. 2. A material that had different optical properties compared to the background was used to print the kidneys.

FIG. 3 shows the mouse phantoms that were 3D printed using the surface profile shown in FIG. 2B. Referring to FIG. 3, from left to right, the first mouse was printed without any inhomogeneities and was used for calibration. The second mouse was printed with highly absorbing inhomogeneities of black ABS in the shape of the kidneys. The third mouse, halted midprint, shows the location and quality of the absorbing inhomogeneities. The fourth mouse was printed with highly scattering inhomogeneities of white ABS in the shape of the kidneys. The fifth mouse was also halted midprint to examine the location and quality of the highly scattering inhomogeneities. The raft was carefully removed before imaging, and a sharp knife was used to remove excess support material on the bottom.

Printing a volume of some material completely enclosed by another volume of a different material is not typically done in 3D printing, although all 3D printers that can print with multiple materials have this capability. Two STL files were generated in MATLAB using the Digimouse atlas: one with the skin surface profile only and the other with both the skin and kidneys surface profiles. The first STL file only was used to generate the homogeneous printed mouse which was used for calibration. Both STL files together were used to generate the printed mice with inhomogeneities in the shape of the kidneys. This was done by placing both surface profiles at the same location on the build plate in the MakerBot software and designating a different extruder to each surface. When the STL files are sliced, the result is a single 3D volume with a different material placed within the volume of the kidneys. If the STL file containing the skin and kidneys surface profiles only was used, empty space instead of material would be present at the location of the kidneys. This type of print would be useful for fluorescence imaging experiments, for example, where a fluorophore in solution could be injected into the cavity.

The data set captured from the homogeneous printed mouse was used to calibrate the data captured from the printed mice with inhomogeneities using $$y_i = y_i^{uncal} \frac{y_i^{comp}}{y_i^{base}}, \quad (1)$$

where i represents the ith component of the data vector, $y_i^{base}$ is raw data captured from the homogeneous mouse, $y_i^{comp}$ is the forward solution data for the homogeneous mouse, and $y_i^{uncal}$ is raw data captured from the mouse with inhomogeneities in the shape of the kidneys. For this work, the forward solution is the numerical solution to the diffusion equation at the detector positions due to excitation by the sources. Note that the calibration was done component by component, constituting unique calibration of every detector-source pair. Equation (1) is particularly convenient for calibrating data in the frequency domain (which was done here), as the camera response is contained within both $y_i^{uncal}$ and $y_i^{base}$ and is canceled out. The primary purpose of this calibration is to remove variations in the amplitude and phase of the measured data that are not described by the numerical model. The validity of this calibration deteriorates if the size and position of the uncal and base objects vary; however, it is ideal for 3D printed objects of the same shape as long as they are placed carefully at the same position on the imaging platform. For a live mouse experiment this type of calibration becomes possible with 3D printing because a homogeneous phantom can be printed in the shape of the live mouse from the surface data acquired from the 3D line scan. This removes the need to calibrate through optimization based inversion and will allow better calibration of experimental data than what has been possible previously with live mice, likely resulting in higher quality images.

In the time domain and for homogeneous scatter, the photon flux density, $\phi(r,t)$ (W/mm2), satisfies the diffusion equation $$\frac{1}{c}\frac{d}{dt}\phi(r, t) - D\Delta^2\phi(r, t) + \mu_a\phi(r, t) = S(r, t), \quad (2)$$

where r denotes the position, $\mu_\alpha$ (mm$^{-1}$) is the linear absorption coefficient, $D=1/[3(\mu_\alpha+(1-g)\mu_s)]$ (mm) is the diffusion coefficient, $\mu_s$ is the linear scattering coefficient, g is the mean cosine of the scattering angle accounting for anisotropy, c is the speed of light in the medium, and S(r, t) is the photon source. This equation can be solved analytically for the transmitted photon flux density in an infinite slab geometry by first assuming that all incident photons are initially scattered at a depth $z_o=1/[(1-g)\mu_s]$, or $z_o=1/\mu'_s$, and placing point image sources such that $\phi(r, t)=0$ on an extrapolated slab boundary [29]. We will define one surface of the slab as being at z=0. We then define the transmittance at the z=d boundary, where d is the thickness of the slab, as the magnitude of the current density from Fick's law in cylindrical coordinates, where the current density $J(\rho, d, t)$ is given by $$J(\rho,d,t)=-D\nabla\phi(\rho, z,t) \quad (3)$$

with $\phi(\rho,z,t)$ the Green's function solution to Eq. (2). Using the discrete dipole approximation to enforce a zero flux boundary in a slab geometry, and retaining four dipoles, the transmittance $T(\rho, d, t)$ through a detector aperture of radius $\rho_o$ is $$T(\rho, d, t) = 4\pi Dct\left[1 - \exp\left(\frac{\rho^2}{4Dct}\right)\right]T_o(d, t) \quad (4)$$

where $T_o(d,t)$ is a function containing the dipole information and is given by $$T_o(d, t) = (4\pi Dc)^{-3/2}t^{-5/2}\exp(\mu_a ct) \quad (5)$$
$$\left\{(d-z_o)\exp\left[-\frac{(d-z_o)}{4DCT}\right] - (d+z_o)\exp\left[-\frac{(d+z_o)}{4DCT}\right] + \right.$$
$$\left.(3d-z_o)\exp\left[-\frac{(3d-z_o)}{4DCT}\right] - (3d+z_o)\exp\left[-\frac{(3d+z_o)}{4DCT}\right]\right\}$$

A simplified solution for Eq. (4) can be found by taking the two-term Taylor expansion with respect to $\rho$ before integrating across the detector aperture.

A gated measurement was performed on an 8 cm by 8 cm 3D printed slab of ABS with d=0.5 cm using the setup shown in FIG. 1. The data were fit to the convolution of the camera response and Eq. (4) by finding the minimum mean square error (MMSE) for various $\mu'_s$ and $\mu_\alpha$. The estimated scatter and absorption parameters at 633 nm were $\mu'_s=1.43$ mm$^{-1}$ and $\mu_\alpha=0.0018$ mm$^{-1}$, respectively, which are close to the values found in other works. These parameter estimates were used for calibration and as the initial values in the reconstruction. The optical scatter and absorption characteristics of ABS are close to what is found in tissue, showing that these phantoms are ideal for evaluating and developing whole animal optical imaging methods.

In DOT, a numerical model describes the propagation of modulated incoherent light through tissue using the diffusion equation, and the absorption ($\mu_\alpha$) and scatter ($\mu'_s$) parameters are reconstructed as a function of position from boundary measurements using an inverse solver. The inverse problem is ill-posed, and the challenge resided in finding the global minimum of an objective function. TOAST++, an open-source collection of libraries for sparse matrix algebra and finite-element analysis, can be used to solve nonlinear inverse problems such as DOT. It should be recognized that other optical imaging modalities besides DOT could be used to image phantoms.

Figure 4:
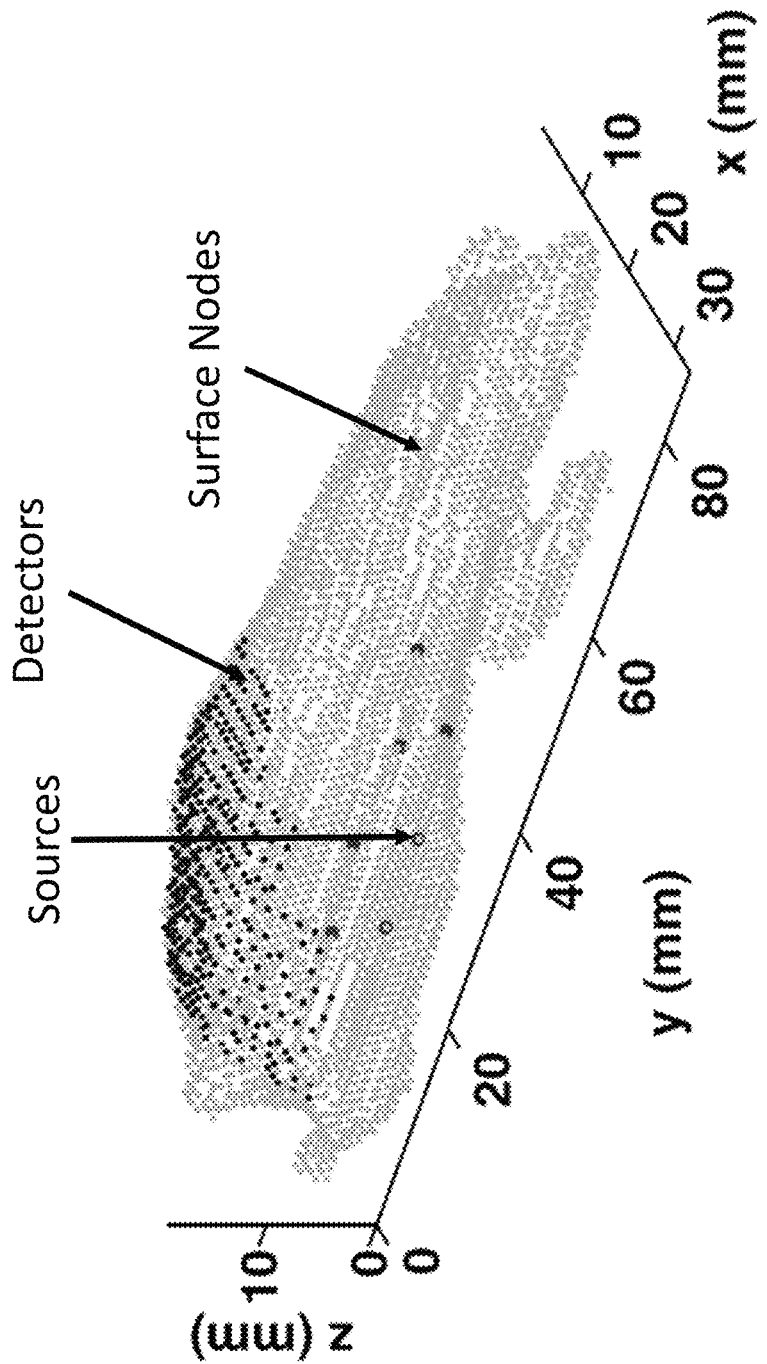
FIG. 4 shows the source and detector positions on the mouse phantom boundary that were used to capture data for optical imaging of the kidneys. These positions were determined using a 3-D laser line scanner.

Boundary data from the printed mouse with highly scattering inhomogeneities in the shape of the kidneys was captured using the experimental setup shown in FIG. 1. The data were calibrated according to Eq. (1) and imported into the TOAST++ environment in MATLAB, along with the source and detector positions obtained using the 3D line scan. An unstructured finite element mesh was generated using TetGen with 22,489 nodes (4881 surface nodes) from a subset of the Digimouse data. Alternatively, the 3D line scan could have been used to generate the mesh, as we have done previously for imaging mice where the 3D surface profile is not known, however, the mesh generated from the Digimouse data is more accurate as it was used to print the mouse. For reconstruction, images were formed on a Cartesian grid with voxel size (1 mm)$^3$ and a nonlinear conjugate gradient iterative solver was used with first-order Tikhonov regularization. The hyperparameter ($\tau$) that weights the penalization imposed by the regularization was set to $10^{-5}$, a relatively small number. Using modulation frequency data at 36 MHz, $\mu_\alpha$ and $\mu'_s$ were simultaneously reconstructed. Data from seven source positions on the bottom and 346 detector positions on the top of the printed mice were used (see FIG. 4), giving 2422 measurements. Each source or detector position in 3D space is defined by a Cartesian coordinate (x,y,z). The data, which was captured in the time domain, was low-pass filtered and then transformed to the frequency domain with a fast Fourier transform. Two outlier data points were removed. A relatively low modulation frequency was used because the calibrated detected phase data were found to most closely match simulated forward data at this frequency. Using a 3.47 GHz Intel X5690 with 96 GB RAM, the reconstruction converged in 20 iterations lasting 1.3 h, where convergence is five consecutive iterations in which the change in the objective function is less than 1% of the mean of the five largest objective function reductions.

FIGS. 5A through 5D show the reconstructed three dimensional images of the printed mouse with highly scattering inhomogeneities in the shape of the kidneys. FIG. 5A shows the $\mu_\alpha$ mesh cross section at the z=15 mm plane. FIG. 5B shows the $\mu_\alpha$ isosurface. FIG. 5C shows the $\mu'_s$ mesh cross section at the z=16 mm plane. FIG. 5D the $\mu'_s$ isosurface. As expected for the highly scattering inhomogeneities, $\mu_\alpha$ is small, and $\mu'_s$ is large compared to the background values. Comparing to FIG. 2(b), the reconstructed $\mu_\alpha$ shows the size and location of the kidneys more accurately than the reconstructed $\mu'_s$, likely because the large contrast between the scattering inhomogeneities and the background made convergence to the exact solution of $\mu'_s$ more difficult. These results show that it is possible to image inhomogeneities in 3D printed phantoms using DOT and that these phantoms are a useful tool for evaluating and developing DOT experimental setups and algorithms.

Thus a mouse atlas can be used to print geometrical replicas of mice with inhomogeneities in the shape of the kidneys, but other atlases could be used to print other objects of interest, such as a human breast or brain with inhomogeneities in the shape of tumors. Objects with more complicated inhomogeneities could be used for general image evaluation, such as a bar pattern for determining spatial resolution. Cavities can be placed within the object that can be filled with a fluorescent solution using a syringe, useful for evaluations of fluorescence diffuse optical tomography. Progress in bioprinting, the printing of complex 3D functional living tissues from biocompatible materials, cells, and supporting components, could enable the fabrication of extremely realistic phantoms. Shells can be printed using clear resins to contain conformable objects (such as a mouse brain) so that the 3D surface profile is known, avoiding the need for the 3D topography laser line scan. For mouse or animal imaging, the surface profile that is captured during a DOT experiment can be used to print a replica of the subject with known optical parameters that can be used for calibration, allowing for better image reconstructions of mice than what have previously been possible.

Although there are broad applications of 3D printed optical phantoms due to the versatile nature of 3D printing, there are restrictions due to the limited materials available and their static optical properties. One solution to this problem is to fabricate molds using 3D printing. These molds can then filled with an epoxy resin with designed optical properties to create phantoms. Although useful for creating molds, placing complex inhomogeneities becomes difficult with this method compared to 3D printing phantoms and inhomogeneities directly with multiple materials. This problem of static optical properties may be addressed by adding varying amounts of India ink, Intralipid, or polystyrene beads to ABS or an equivalent printing material to control the optical properties, although this must be done carefully to not disrupt the 3D printing process. Additionally, fluorescent chemicals could be added to the printing material in order to print fluorescent inhomogeneities.

From the foregoing description, it is clear that 3D printing is useful for creating realistic tissue-like phantoms with complicated geometries and inhomogeneities for evaluating and developing optical imaging methods, such as DOT. 3D printing is an effective tool (and perhaps in some cases the only tool) for creating complicated phantoms with inhomogeneities for imaging. The mouse phantoms fabricated here were designed for imaging with DOT, but all optical imaging methods can benefit from customizable 3D printed phantoms. In addition to fabricating phantoms, 3D printing can be used to create optics equipment, lenses, and optical fibers, and is useful for customizing experimental setups, making 3D printers a useful addition to any imaging or optics lab.

In other experiments leading to this disclosure, Mie theory was used to design the optical properties (specifically, the scattering coefficient $\mu'_s$) of a printed phantom, providing a simple and effective method for tuning the optical properties. First, Mie theory was used to calculate the concentration of polystyrene microspheres to be mixed with a clear printing resin in order to achieve a target $\mu'_s$. Stereolithography was then used to print a phantom from this beads-resin mixture. It has been demonstrated in experiments of this disclosure that it is possible to design the optical properties of a printed mouse phantom using this method. A fluorescent inhomogeneity within the mouse phantom (simulating a tumor or organ stained with a targeted fluorescent imaging agent) was imaged using FODT. FODT is a whole animal optical imaging method, useful, for example, for finding tumors, determining pharmacokinetic rates, and imaging the whole brain. In this detailed description, quantitative imaging of an inhomogeneity, analogous to determining the fluorophore concentration in deep tissue, is shown, demonstrating the usefulness of the printed phantoms for developing FODT and other optical imaging methods for biomedical applications.

Figure 6:
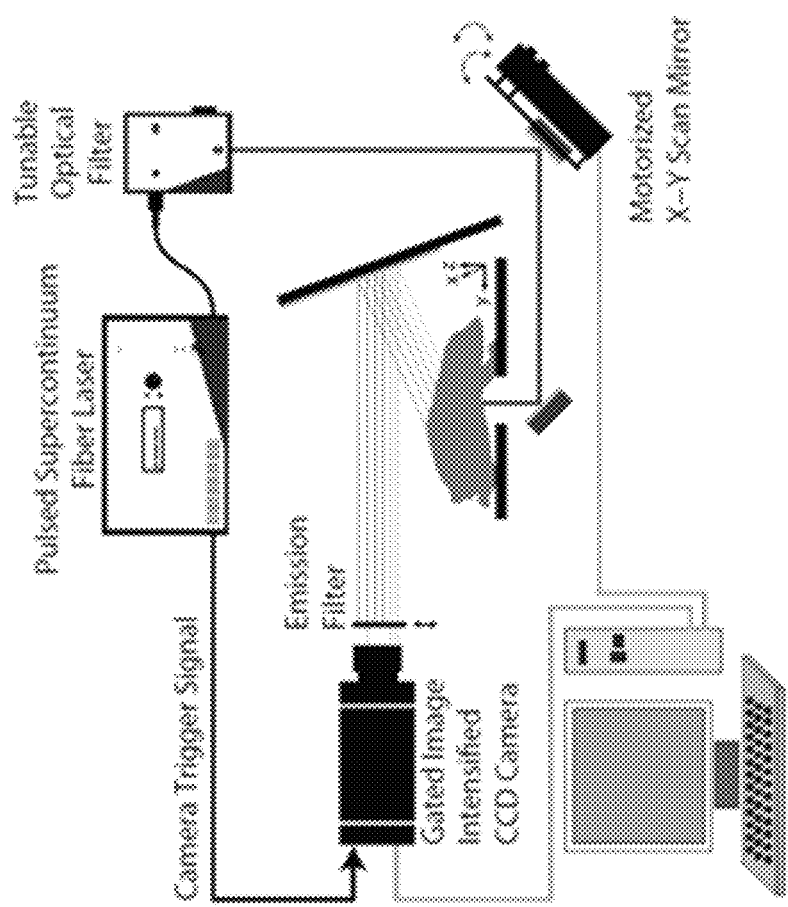
FIG. 6 is a schematic representation of a non-limiting experimental setup used to collect data for optical imaging. An EXR-20 and VARIA (NKT Photonics) output pulses at 20 MHz (allowing fluorescence decay between pulses). Transmitted highly scattered light is detected by a gated, intensified CCD camera (Roper PIMAX). An emission bandpass filter allows collection of fluorescence. A motorized X-Y scan mirror (Zaber) changes the source position before each measurement.

FIG. 6 shows the experimental set up used for acquiring data for optical imaging of the phantom designed using Mie theory. The setup in FIG. 6 is similar to the one shown in FIG. 1. Referring to FIG. 6, an EXR-20 generates a pulsed supercontinuum that is filtered by a VARIA tunable bandpass filter gives picosecond pulses tunable from 485-850 nm with 10-100 nm variable bandwidth. A photodiode measuring the fiber seed pulse allows triggering of the gated camera, constituting a time-domain measurement of the medium response.

Mie's solution to Maxwell's equations describes the scattering of a plane wave in a homogeneous medium by a sphere with known diameter and refractive index. The fields are written as an expansion in vector spherical harmonics, and coefficients describing the amplitudes of the scattered and internal fields can be calculated from the boundary conditions. The sphere's scattering cross section, $\sigma_s$, and anisotropy, g, can be written in terms of these coefficients. Then, assuming that the spheres are far apart, $\mu'_s = \sigma_s C(1-g)$, where C is the concentration of spheres [20]. We fabricated a 3D printed material with known $\mu'_s$ by mixing polystyrene microspheres (Bangs Laboratories, diameter 0.76 mm, refractive index ~1.59) with a clear printing photopolymer resin. By varying the concentration of microspheres C, $\mu'_s$ can be designed to match that of a target tissue. In terms of the sphere volume fraction fv, C=fv/V, where V is the volume of a single sphere. We prepared 100 mL solutions with fv=0.005 by mixing 1.67 mL of fv=0.3 bead solution in water with 98.33 mL of clear printing resin. The density of the water, microspheres, and clear resin are all close to 1 g/mL.

A Formlabs 3-D printer was utilized, and the bead-resin mixture was placed in the printer's resin tank. The Formlabs clear resin is a mixture of methacrylic acid esters and a photoinitiator, and has a refractive index similar to acrylic glass (~1.49). The printer uses stereolithography to form each layer of the 3D print, where a UV laser cures the photopolymer resin at desired positions. Stereolithography allows the polystyrene microspheres to be "frozen" in place, and is preferred to fused deposition modeling where the polymer would be fed through a heated nozzle, possibly influencing the diameter distribution of the microspheres such that $\mu'_s$ could not be reliably designed with Mie theory. $\mu'_s$ and $\mu_a$ were estimated using the setup shown in FIG. 6. The temporal response of a 7×7×0.75 cm slab printed using the bead-resin mixture was measured and fit to an analogous analytical solution to the diffusion equation in an infinite slab geometry [7, 21]. The estimated $\mu'_s$ from the fit is compared to the theoretical result calculated using Mie theory in FIG. 2(b). The mean experimental error was 6.4%, showing close agreement with the Mie theory prediction. The absorption was found to not vary much with wavelength, and had a mean value of 0.007 mm$^{-1}$. g was calculated from Mie theory, and was approximately 0.9. For this initial work, we used a low sphere volume fraction (fv=0.005) to ensure we did not disrupt the stereolithography, resulting in a $\mu'_s$ that is similar to breast tissue (~1 mm$^{-1}$) [22]. From observations of the quality of the prints and other related experiments, we expect that the percent fill (and thus the amount of scatter) could be significantly increased without disrupting the printing process.

Figure 7A:
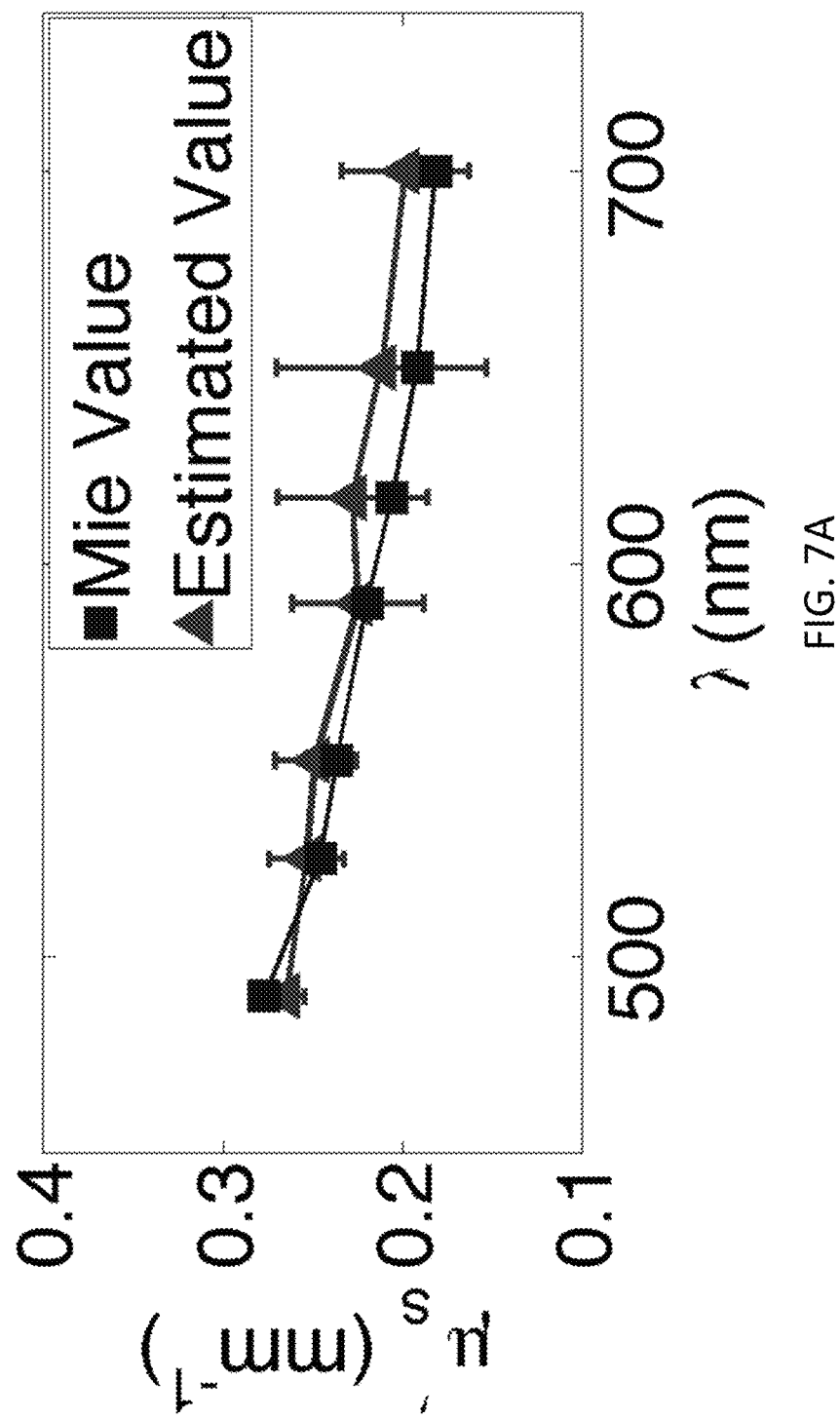
FIG. 7A shows the $\mu'_s$ spectrum of a printed polystyrene beads and resin mixture, calculated using Mie theory and estimated from measurements of 3D printed slabs.
Figure 7B:
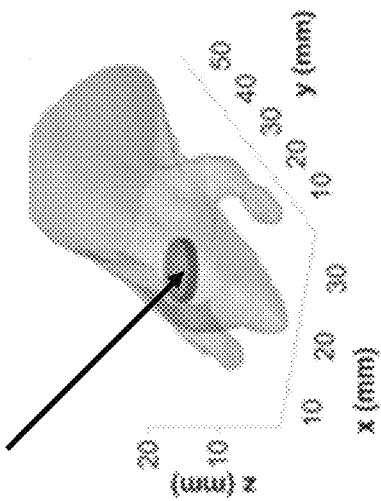
FIG. 7B shows the isosurface used to generate the STL file for 3D printing. The Digimouse atlas was used to generate the isosurface. A cylindrical cavity for placing chemicals was created in the region of the brain.
Figure 7C:
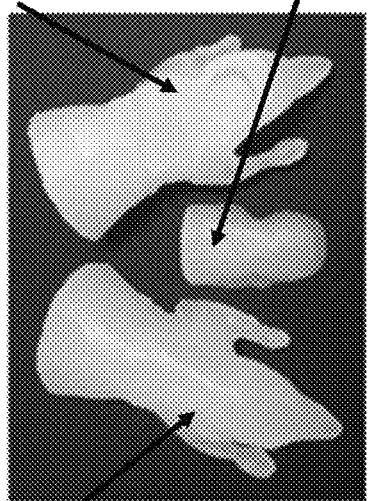
FIG. 7C shows phantoms with controlled optical properties that were fabricated using 3D printing and the isosurface in FIG. 7B. A removable printed piece gives access to the cavity inhomogeneity, allowing chemical solutions to be placed within the phantom. The printed material does not react with most solvents.

The same bead-resin mixture described above was used to print an anatomically realistic mouse phantom using the Digimouse atlas, which contains the surface profile of all major mouse organs. A simple cylindrical cavity inhomogeneity was placed in the general location of the brain, as seen in FIG. 7B. The cylindrical cavity is intended to be a proof of concept, and could easily be replaced using the brain surface profile, creating a more anatomically realistic inhomogeneity. FIG. 7C shows the printed phantom in this case.

Frozen aliquots of the fluorescent protein EGFP (484 nm excitation, 507 nm emission) were thawed and buffer exchanged into phosphate buffered saline (10mMphosphate buffer, 2.7 mM KCl, and 137 mM NaCl, pH 7.4) using a 10 kDa spin filter, and the protein concentration was assessed using the bicinchoninic acid assay. Prior to use in imaging analysis, the protein was diluted to 10 mM in a solution of microspheres and water such that fv=0.005, to match the background scatter. The diluted protein was injected into the phantom cavity inhomogeneity to be imaged.

In FODT, a forward model describes the propagation of modulated incoherent light through tissue and the $\mu'_s$, $\mu_a$, and fluorescent parameters are reconstructed as a function of three dimensional position from boundary measurements using an inverse solver. We use the diffusion approximation to the radiative transfer equation to simply the forward model to coupled diffusion equations given by $$\nabla \cdot [D_x(r)\nabla \phi_x(r, \omega)] - \left[\mu_a(r) + \frac{j\omega}{c}\right]\phi_x(r, \omega) = -S_x(r; \omega), \quad (6)$$

$$\nabla \cdot [D_m(r)\nabla \phi_m(r, \omega)] - \left[\mu_a(r) + \frac{j\omega}{c}\right]\phi_m(r, \omega) = -\phi_x(r, \omega)S_f(r; \omega), \quad (7)$$

where r denotes the position, $\phi(r, \omega)$ (W/mm$^2$) is the photon flux density, $\omega$ is the angular modulation frequency, $D=1/[3(\mu'_s+\mu_a)]$ (mm) is the diffusion coefficient, c is the speed of light in the medium, the subscripts x and m, respectively, denote parameters at the fluorophore excitation and emission wavelengths, $\lambda_x$ and $\lambda_m$, $S_x$ (W/mm$^3$) is the excitation source term, and $S_f = \eta(1+j\omega\tau)^{-1}$ (mm$^{-1}$) is the fluorescence source term. The fluorescence parameters are the lifetime $\tau$ (ns) and the fluorescence yield $\eta = \eta_q\mu_{a_f}$ (mm$^{-1}$), where $\eta_q$ and $\mu_{a_f}$ are the quantum yield and absorption of the fluorophore, respectively. Eq. (6) and Eq. (7) were solved on an unstructured finite element method (FEM) mesh.

Figure 8A:
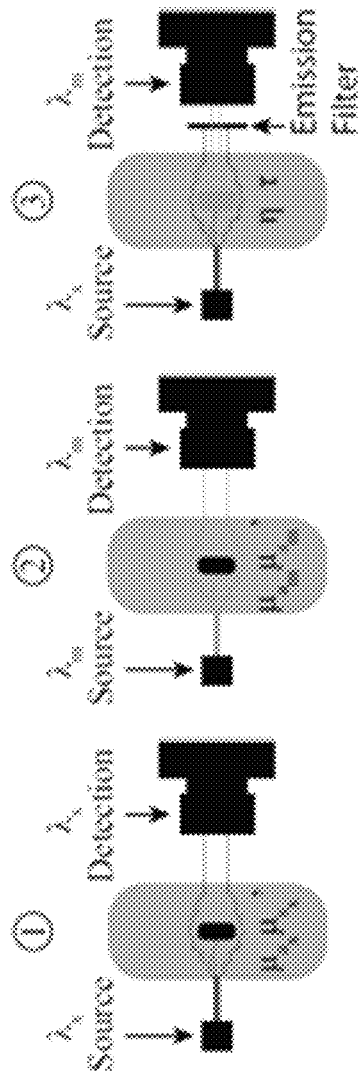
FIG. 8A shows a standard FODT measurement scheme. Three measurements at various wavelengths are required in order to form 3D images of the optical parameters.

In an FODT experiment, three boundary measurements are needed, as depicted in FIG. 8A. Measurements are made with the source tuned to $\lambda_x$ and $\lambda_m$ are used to reconstruct $\mu'_{s_x}$, $\mu_{a_x}$, $\mu'_{s_m}$, and $\mu_{a_m}$ using Eq. (1). These parameters characterize light propagation in the medium, and are required for the fluorescence reconstruction. The medium is then excited at $\lambda_x$, and a bandpass filter is used for boundary measurements at $\lambda_m$. This final data set is used to reconstruct the fluorescence parameters of the medium using Eq. (2). Following this procedure, the EXR- 20 was tuned to 490 nm with a 10 nm bandwidth for $\lambda_x$ (17 mW average power), and to 525 nm with 10 nm bandwidth for $\lambda_m$ (9 mW average power). An emission bandpass filter centered at 525 nm with 25 nm bandwidth (EO 87-801) was placed in front of the camera when collecting the fluorescence emission.

Figure 8B:
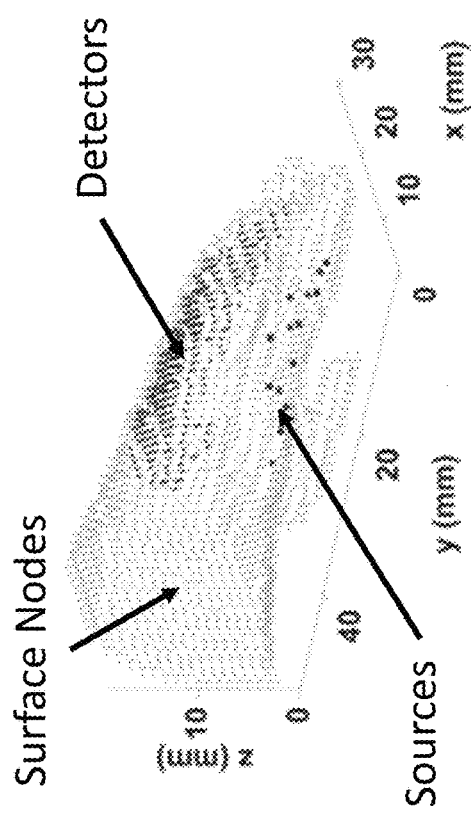
FIG. 8B shows 15 sources (bottom dots) and 322 detectors (top smaller dots) positions on the Digimouse surface nodes (green) giving rise to 4830 measurements.

The boundary measurements were repeated for each source position in FIG. 8B, where the detectors are CCD camera pixels. A 3D topography laser line scanner was used to project the CCD pixels to detector positions on the surface, as we have described previously. Pseudo-CW data was captured for the FODT reconstruction using a 200 ms integration time, allowing reconstruction of $\eta$ but not $\tau$. Calibration is necessary to account for source and detector coupling to the scattering medium, relating synthetic numerical data to experimental data. The uncalibrated experiment data $y_k^{uncal}$, where k is the data index, was calibrated as we have done previously. Briefly, the phantom cavity inhomogeneity was filled with a mixture of polystyrene microspheres and water such that fv=0.005, making the phantom approximately homogeneous. The measurements in FIG. 8A were repeated with the homogeneous phantom, resulting in three baseline measurements $y_k^{base}$. Corresponding synthetic data $y_k^{syn}$ was generated using the known homogeneous $\mu'_s$ and $\mu_\alpha$ and the calibrated data $y_k^{cal}$ was calculated as $y_k^{cal} = y_k^{uncal}[y_k^{syn}/y_k^{base}]$. For the fluorescence data set, the base data was subtracted to remove filter bleed through. The resulting three calibrated data sets were used for FODT reconstructions.

An image reconstruction algorithm was used. Briefly, a Bayesian nonlinear optimization framework allows incorporation of a priori information as well as a forward model into a maximum a posteriori (MAP) estimate. The spatial correlation between image voxels is modeled by a generalized Gaussian Markov random field (GGMRF). The problem becomes the minimization of cost functions and it is solved by the iterative coordinate descent (ICD) algorithm, described by $$\hat{x}_l = \underset{\tilde{x}_l}{\operatorname{argmin}} \left[ \|y - f(\tilde{x}_l)\|_\Lambda^2 + \frac{1}{\rho \sigma^\rho} \sum_{j \in N_i} b_{ij} |\tilde{x}_l - x_j|^\rho \right] \quad (8)$$

where x is the image to be reconstructed, subscript i represents the voxel being updated, $\overline{x}_l$ is the updated or reconstructed value, $\tilde{x}_l$ is the initial or current value to be updated, y is a vector of length N representing the measurements (calibrated experimental data—here N=4830), f(x) is the solution to the forward model described by Eq. (6) and Eq. (7), for assumed x, and for an arbitrary vector w, $\|w\|_\Lambda^2 = w^H \Lambda w$, where H denotes Hermitian transpose with $\Lambda^{-1} = \text{diag}[|y_1| \ldots |y_p|]$. The form of $\Lambda$ implies that the measurements are uncorrelated. The prior model, the GGMRF, constitutes regularization and is characterized by $\sigma$ and $\rho$, which are constants representing scale and shape parameters for the distribution, respectively, and $b_{ij}$, which provides a local 26-neighborhood ($N_i$) weight. Here we use $\rho=2$, which gives a Gaussian prior model.

Figure 9B:
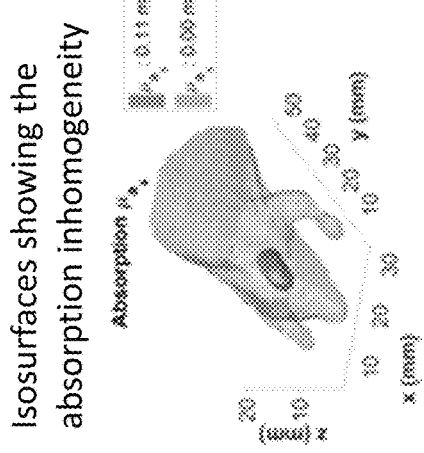
FIG. 9B shows isosurfaces generated using the $\mu_{a_X}(r)$ image. The EGFP inhomogeneity is clearly visible.
Figure 9D:
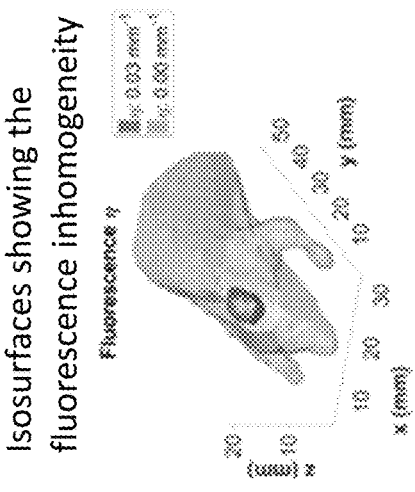
FIG. 9D shows isosurfaces generated using the $\eta(r)$ image. The EGFP inhomogeneity inhomogeneity is clearly visible.
Figure 9A:
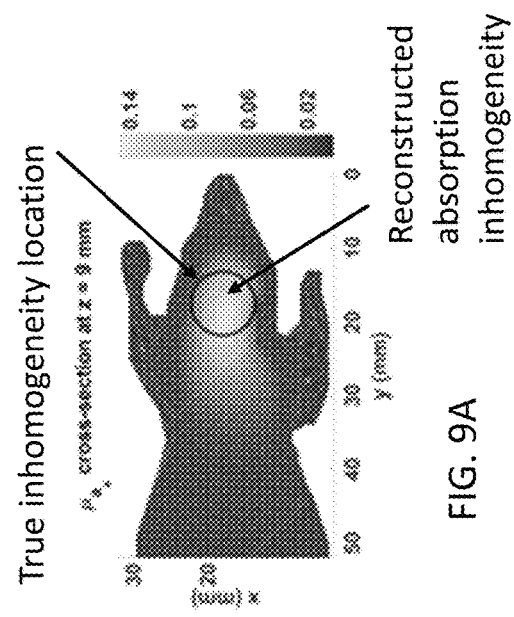
FIG. 9A shows a $\mu_{a_X}(r)$ cross section from the reconstructed image at the peak value (z=9 mm plane). Data was collected from the printed mouse phantom with an EGFP inhomogeneity.

The two calibrated data sets at $\lambda_x$ and $\lambda_m$ were used to reconstruct $\mu_{\alpha_x}(r)$ and $\mu_{\alpha_m}(r)$. $\mu'_s(r)$ was assumed known and homogeneous from FIG. 7A and was not reconstructed. The validity of this assumption is apparent in the results. The reconstructed $\mu_{\alpha_x}(r)$ cross section is shown in FIG. 9A, and its isosurface is shown in FIG. 9B. As expected, the absorption increases in the region of the fluorescent inhomogeneity. For EGFP, we expect that $\mu_{\alpha_x} = \ln(10) \, \epsilon_x C_{EGFP} = 0.129$ (mm$^{-1}$), where $\epsilon_x$ is the molar absorptivity (5600 1/M/mm) and $C_{EGFP}$ is the concentration (10 mM) of EGFP. From FIG. 9A, it can be seen that $\mu_{\alpha_x}(r)$ was quantitatively reconstructed in the region of the inhomogeneity. For brevity the reconstructed $\mu_{\alpha_m}(r)$ is not shown, but its value was lower in the region of the fluorescent inhomogeneity.

Figure 9C:
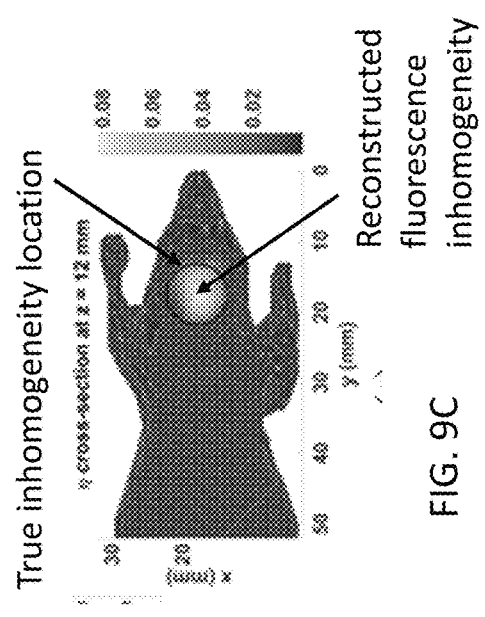
FIG. 9C shows a $\eta(r)$ cross section from the reconstructed image at the peak value (z=12 mm plane). Data was collected from the printed mouse phantom with an EGFP inhomogeneity.

The calibrated fluorescence data excited at $\lambda_x$ and measured at $\lambda_m$ was used to reconstruct $\eta(r)$ using the reconstructed $\mu_{\alpha_x}(r)$ and $\mu_{\alpha_m}(r)$ and homogeneous $\mu'_s(r)$. The reconstructed $\eta(r)$ cross section is shown in FIG. 9C, and its isosurface is shown in FIG. 9D. Comparing to the surface profile used to print the phantom in FIG. 7B, the size and location of the fluorescent inhomogeneity was accurately reconstructed despite some error in the reconstruction of $\mu_{\alpha_x}$. Quantitatively, we expect that $\eta = \eta_{EGFP} \mu_{\alpha_x} = 0.0774$ (mm$^{-1}$), where $\eta_{EGFP}$ is the quantum yield of EGFP (0.6), and we see that this value was reconstructed in the region of the inhomogeneity. The fractional error can be calculated using $|\Sigma_i^N \eta_{target}(r_i) - \Sigma_i^N \eta(r_i)|/\Sigma_i^N \eta(r_i)$, where $\eta_{target}(r)$ is the target fluorescence image. The reconstruction results support the validity of the $\mu'_s$ spectrum in FIG. 2(b). Note that only the measured data was calibrated and that the reconstruction algorithm converged to a quantitative result.

The reconstruction described above includes the regularization term $\sigma$, which acts as a low pass filter to prevent overfitting when solving the ill-posed inverse problem. As $\sigma$ is increased, both the prior term weight in Eq. (8) and the amount of smoothing are reduced, causing the reconstructed values change. It is desirable for $\sigma$ to be large to minimize smoothing, but small enough to ensure that the image does not become distorted due to overfitting. Here, we found that the values of $\sigma$ which gave quantitatively correct values for $\mu_{\alpha_x}$, $\mu_{\alpha_m}$, and $\eta$ corresponded to the most accurate images of the inhomogeneity size and location. These values of $\sigma$ were not the maximum values that resulted in no distortion of the images due to overfitting, as would otherwise be used if the quantitatively correct values for $\mu_{\alpha_x}$, $\mu_{\alpha_m}$, and $\eta$ were unknown. Thus, using known quantitative information allows improved regularization, resulting in better reconstructed images. Alternatively, if the size and location of the inhomogeneity are known or can be estimated, quantitative information can be extracted, useful for biomedical applications.

Mie theory can describe the absorption of a medium, allowing straightforward extension of our method to design both the $\mu'_s$ and $\mu_\alpha$ of printed phantoms with the addition of absorbing agents, such as India ink or nigrosin to the photopolymer resin. Black photopolymer resins are available, leading us to believe the absorption (and scatter) could be tuned over a very wide range on commercial 3D printers without disrupting the printing process. Fluorescent chemicals such as quantum dots could also be added to the photopolymer resin.

From this detailed description, it can be seen that in this disclosure a new method has been demonstrated for fabricating phantoms using 3D printing that allows design of the phantom's optical properties and geometry, for example, to match a particular subject. A mouse phantom was fabricated and imaged and FODT can be used to obtain quantitative information, demonstrating the usefulness of the printed phantoms for developing FODT. The methods of this disclosure can be used to create phantoms with different geometries, for other imaging modalities, and for calibration of data captured from live animals. Fundamentally, with improved 3D printing technology, the methods of this disclosure could allow a complete phantom to be printed from multiple materials with optical properties that match those of the respective tissues. In principle, an exact replica of a target object, such as tissue, could be fabricated and used for developing optical imaging methods.

The phantoms described within this disclosure may be designed for almost any optical imaging modality. For example, phantoms with micrometer and smaller features could be printed for microscopic and related methods that rely on the coherence of light, such as optical coherence tomography or OCT. Larger phantoms could also be adapted for photoacoustic imaging, because the acoustic properties of the phantom are modified in addition to the optical properties.

Based on the above description, it is an objective of this disclosure to describe an optically heterogeneous phantom structure for use in optical imaging techniques. The optically heterogeneous phantom structure of this disclosure includes an external shape simulating an object to be subjected to an optical imaging technique, the external shape defining an external surface that encloses an internal volume of the external shape. The phantom structure further includes an optically heterogeneous material filling the internal volume and having heterogeneous optical properties for simulating at least one optical parameter of at least one region within the object. The optically heterogeneous material contains at least first and second materials having different optical properties, the second material being surrounded by at least the first material and simulating inhomogeneities of the object, wherein at least one of the at least first and second materials contains at least a first additive so as to have at least one optical parameter that is different for the first material and the second material. The phantom structure of this disclosure is formed by 3D printing and stereolithography to sequentially form the external shape of the phantom structure a layer at a time, to be substantially watertight at the external surface thereof, and to be substantially free of air gaps within the internal volume thereof.

In a specific embodiment of the methods of this disclosure, an external shape was formed using the Digimouse atlas. This surface was filled with multiple materials using 3D printing. The first material was natural ABS, and simulated the optical properties of the background tissue. The second material was white ABS and simulated the optical properties of the kidneys. These materials are well known to those in the art of 3D printing. This second material was thus surrounded by the first material, and simulated the kidneys such that light within the phantom propagated in a similar manner as in a real mouse. Instead of ABS, the two materials could be formed, for example, from mixtures of clear resin and two different densities of additives. The density of the additives would be calculated such that the light within each of the two materials propagated in a way similar to that of the tissue it was designed to mimic. Of course, more than two different densities of additives could be used such that the volume is filled with more than two materials.

In some embodiments of the phantom structure, the first material is a cured clear photopolymer resin. In some embodiments of the phantom structure, the first material contains a cured clear photopolymer resin and at least the first additive. In some embodiments of the phantom structure, the second material comprises a cured clear photopolymer resin and at least the first additive. In some embodiments, the second material is located more than two millimeters below the external surface of the phantom structure.

It should be recognized that in the phantom structures of this disclosure, the cured clear photopolymer resin can be a mixture of methacrylic acid esters and a photoinitiator. In the phantom structures of this disclosure, examples of the optical parameter simulated include, but are not limited to, a scattering property, an absorption property, and a fluorescent property. Examples of the first additive in the phantom structures of this disclosure include, but are not limited to, India ink, Intralipid, nigrosine, polystyrene microspheres, fluorescent proteins, and quantum dots.

It should be recognized that in the optically heterogeneous phantom structures described in this disclosure, the region simulated by the second material within the object can be a tissue within a living body. In some embodiments, the tissue can be an internal organ. Non-limiting examples of such internal organs include heart, brain, kidneys, lungs, liver, skeleton, and vascular structure of the living body.

Some embodiments of the phantom structure can include at least a third material that comprises at least the first additive or a second additive so as to have at least one optical parameter that is different from the first material and optionally different from the second material.

It is also an objective of this disclosure to describe a method of producing the optically heterogeneous phantom structure detailed above. The method includes selectively depositing precursors of the first and second materials by 3D printing so that the precursor of the second material is surrounded by the precursor of the first material within a predetermined internal region of the precursor of the first material; and forming the phantom structure by a 3D printing process and curing the precursors of the first and second materials so that the second material simulates optical properties of the region within the object. In one embodiments of this method, the 3D printing process used to form the phantom structure is stereolithography.

In one embodiment of the method of producing the phantom structures of this disclosure, the first additive is present in an amount in the second material for attaining an optical parameter within the predetermined internal region that emulates the optical parameter of the region within the object. It should be recognized that in some embodiments of the method, the amount of the first additive is analytically calculated using Mie theory. It should be recognized that the amount of the first additive could also be determined empirically. Further, in this method, the precursors of the first and second materials are cured with electromagnetic radiation.

It should be noted that the method of making the phantom structures of this disclosure can include the additional step of performing an optical imaging technique with the phantom structure to test, evaluate, develop, or calibrate optical imaging equipment used in the optical imaging technique.

While the present disclosure has been described with reference to certain embodiments, it will be apparent to those of ordinary skill in the art that other embodiments and implementations are possible that are within the scope of the present disclosure without departing from the spirit and scope of the present disclosure. Thus, the implementations should not be limited to the particular limitations described. Other implementations may be possible. It is therefore intended that the foregoing detailed description be regarded as illustrative rather than limiting. Thus, this disclosure is limited only by the following claims.

The invention claimed is:

1. An optically heterogeneous phantom structure for use in optical imaging techniques, the phantom structure comprising:
   an external shape simulating an object to be subjected to an optical imaging technique, the external shape defining an external surface that encloses an internal volume of the external shape; and
   an optically heterogeneous material filling the internal volume and having heterogeneous optical properties for simulating at least one optical parameter of at least one region within the object, the optically heterogeneous material comprising at least first and second materials having different optical properties, the second material being surrounded by at least the first material and simulating inhomogeneities of the object, wherein at least one of the at least first and second materials contains at least a first additive so as to have at least one optical parameter that is different for the first material and the second material, wherein the phantom structure is formed by 3D printing to sequentially form the external shape of the phantom structure a layer at a time, to be substantially watertight at the external surface thereof, and to be substantially free of air gaps within the internal volume thereof.

2. The optically heterogeneous phantom structure according to claim 1, wherein the first material is a cured clear photopolymer resin.

3. The optically heterogeneous phantom structure according to claim 1, wherein the second material comprises a cured clear photopolymer resin and at least the first additive.

4. The optically heterogeneous phantom structure according to claim 2, wherein the second material comprises a cured clear photopolymer resin and at least the first additive.

5. The optically heterogeneous phantom structure according to claim 3, wherein the cured clear photopolymer resin is mixture of methacrylic acid esters and a photoinitiator.

6. The optically heterogeneous phantom structure according to claim 4, wherein the cured clear photopolymer resin is mixture of methacrylic acid esters and a photoinitiator.

7. The optically heterogeneous phantom structure according to claim 1, wherein the at least one optical parameter is one of a scattering property, an absorption property, and a fluorescent property.

8. The optically heterogeneous phantom structure according to claims 1, wherein the first additive is at least one of India ink, Intralipid, nigrosine, polystyrene microspheres, fluorescent proteins, or quantum dots.

9. The optically heterogeneous phantom structure according to claim 1, wherein the region simulated by the second material within the object is tissue within a living body.

10. The optically heterogeneous phantom structure according to claim 9, wherein the tissue is an internal organ within the living body.

11. The optically heterogeneous phantom structure according to claim 10, wherein the internal organ simulated by the second material is chosen from at least one of the heart, brain, kidneys, lungs, liver, skeleton, and vascular structure of the living body.

12. The optically heterogeneous phantom structure according to claim 1, wherein the second material is located more than two millimeters below the external surface of the phantom structure.

13. The optically heterogeneous phantom structure according to claims 1, further comprising at least a third material that comprises at least the first additive or a second additive so as to have at least one optical parameter that is different from the first material and optionally different from the second material.

14. A method of producing an optically heterogeneous phantom structure, the method comprising:
   selectively depositing precursors of a first material and a second material by 3D printing so that the precursor of the second material is surrounded by the precursor of the first material within a predetermined internal region of the precursor of the first material, the materials comprising at least a first additive so as to have at least one optical parameter that is different from the other material; and
   forming the phantom structure by a 3D printing process and curing the precursors of the first and second materials so that the second material simulates optical properties of the region within the object.

15. The method according to claim 14, wherein the first additive is present in an amount in the second material for attaining an optical parameter within the predetermined internal region that emulates the optical parameter of the region within the object.

16. The method according to claim 15, wherein the amount of the first additive is analytically calculated using Mie theory.

17. The method according to claim 15, wherein the amount of the first additive is determined empirically.

18. The method according to claim 14, wherein the precursors of the first and second materials are cured with electromagnetic radiation.

19. The method according to claim 14, further comprising performing an optical imaging technique with the phantom structure to test, evaluate, develop, or calibrate optical imaging equipment used in the optical imaging technique.

20. The method according to claim 14, wherein the 3D printing process is stereolithography.

21. A method of producing an optically heterogeneous phantom structure, the method comprising:
   selectively depositing precursors of at least first and second materials by 3D printing so that the precursor of the second material is surrounded by the precursor of the first material within a predetermined internal region of the precursor of the first material; and
   forming the phantom structure by a 3D printing process and curing the precursors of the first and second materials so that the second material simulates optical properties of the region within the object.

22. The method of claim 21, wherein the 3D printing process is stereolithgraphy.

* * * * *